United States Patent
Cho et al.

(10) Patent No.: US 7,874,030 B2
(45) Date of Patent: Jan. 25, 2011

(54) DEVICE FOR TRANSFERRING A CRADLE FOR USE WITH A MEDICAL IMAGING EQUIPMENT

(75) Inventors: Zang Hee Cho, Incheon (KR); Cheol Ok Lee, Incheon (KR); Young Bo Kim, Seongnam-si (KR); Ja Weon Yun, Suwon-si (KR); Hyung Jin Ahn, Anyang-si (KR); Dong Sung Kim, Suwon-si (KR); Hong Shim, Suwon-si (KR)

(73) Assignee: Gachon University of Medicine & Science Industry—Academic Cooperation Foundation, Incheon (KR)

( * ) Notice: Subject to any disclaimer, the term of this patent is extended or adjusted under 35 U.S.C. 154(b) by 691 days.

(21) Appl. No.: 11/840,343

(22) Filed: Aug. 17, 2007

(65) Prior Publication Data

US 2008/0045831 A1    Feb. 21, 2008

(30) Foreign Application Priority Data

Aug. 18, 2006    (KR) ...................... 10-2006-0078065

(51) Int. Cl.
- *A61B 6/04* (2006.01)
- *A61B 5/055* (2006.01)
- *A61G 7/08* (2006.01)

(52) U.S. Cl. .......................... 5/601; 5/81.1 HS; 5/943; 378/20; 378/209; 600/415

(58) Field of Classification Search ............ 5/601, 5/600, 611, 81.1 R, 86.1, 81.1 HS, 943; 378/209, 378/208, 20; 600/415
See application file for complete search history.

(56) References Cited

U.S. PATENT DOCUMENTS

| | | | | |
|---|---|---|---|---|
| 3,588,500 A | * | 6/1971 | Koerner .......................... | 5/601 |
| 4,034,224 A | * | 7/1977 | Heavens et al. ............... | 378/20 |
| 4,105,923 A | * | 8/1978 | Hynes, Jr. ..................... | 378/20 |
| 4,475,072 A | * | 10/1984 | Schwehr et al. ............. | 318/602 |

(Continued)

FOREIGN PATENT DOCUMENTS

JP        02-055042    2/1990

(Continued)

*Primary Examiner*—Robert G Santos
(74) *Attorney, Agent, or Firm*—Patterson Thuente Christensen Pedersen, P.A.

(57) ABSTRACT

Embodiments of the present invention may provide a cradle transferring device, which moves and withdraws a cradle to and from an examination table of an MRI apparatus in a PET-MRI hybrid system. The cradle transferring device includes: a cradle, on which a subject lies; a shuttle table supporting the cradle and moving and withdrawing the cradle to and from the examination table of the MRI apparatus; and a cradle receiving member provided on the examination table of the MRI apparatus. The shuttle table is provided with a transfer member for holding and transferring the cradle and a transfer member driving means for reciprocating the transfer member along the shuttle table. The cradle transferring device is further provided with a cradle locking means, which locks the cradle to the examination table after the cradle is moved to the examination table. The cradle transferring device moves the cradle to the examination table of the MRI apparatus and accurately withdraws the cradle from the examination table of the MRI apparatus after the examination in the MRI apparatus.

14 Claims, 15 Drawing Sheets

U.S. PATENT DOCUMENTS

| | | | |
|---|---|---|---|
| 4,641,823 A * | 2/1987 | Bergman | 5/81.1 HS |
| 4,771,785 A * | 9/1988 | Duer | 600/415 |
| 5,808,468 A * | 9/1998 | Bis et al. | 324/318 |
| 6,385,481 B2 | 5/2002 | Nose et al. | |
| 6,493,571 B1 * | 12/2002 | Bis et al. | 600/420 |
| 6,640,364 B1 * | 11/2003 | Josephson et al. | 5/601 |
| 6,782,571 B1 * | 8/2004 | Josephson et al. | 5/601 |
| 7,216,383 B2 * | 5/2007 | Heinl et al. | 5/601 |
| 2001/0003218 A1 | 6/2001 | Schaefer | |
| 2002/0013524 A1 | 1/2002 | Hayashi et al. | |
| 2005/0060804 A1 * | 3/2005 | Heinl et al. | 5/601 |
| 2008/0045831 A1 * | 2/2008 | Cho et al. | 600/415 |

FOREIGN PATENT DOCUMENTS

| | | |
|---|---|---|
| KR | 1999-068038 | 8/1999 |

* cited by examiner

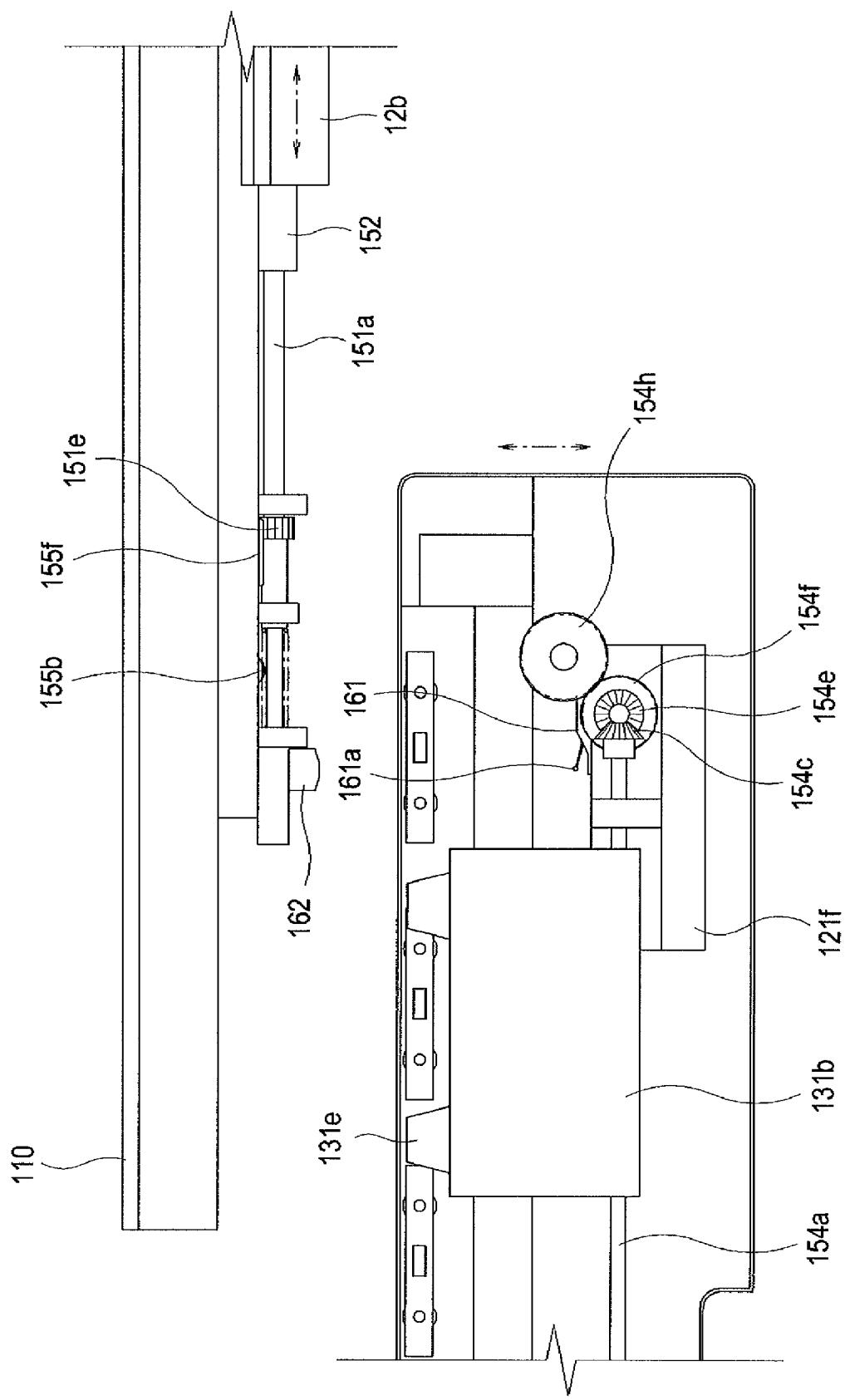

DEVICE FOR TRANSFERRING A CRADLE FOR USE WITH A MEDICAL IMAGING EQUIPMENT

The present application claims priority from Korean Patent Application No. 10-2006-0078065 filed on Aug. 18, 2006, the entire subject matter of which is incorporated herein by reference.

BACKGROUND

1. Field

Embodiments of the present invention may relate to a device for transferring a cradle for use with a medical imaging equipment, and more particularly to a cradle transferring device for moving and withdrawing a cradle, on which a subject lies, to and from an examination table of an MRI apparatus in a PET-MRI hybrid system.

2. Background

A positron emission tomography (PET) apparatus and a magnetic resonance image (MRI) apparatus are widely used to obtain a brain image among medical imaging equipments. The MRI apparatus has the highest spatial resolution among the medical imaging equipments. The PET apparatus can provide various molecular images, which are difficult to be obtained by the MRI apparatus. Recently, "a PET-MRI hybrid system (or PET-MRI fusion image system)" has been developed in the art. The PET-MRI hybrid system can obtain high-resolution anatomic information and molecular information on a brain by integrating the PET apparatus and the MRI apparatus.

FIG. 1 shows a schematic constitution of the PET-MRI hybrid system. The PET-MRI hybrid system 10 provides fusion images on a brain by integrating the information obtained by the PET apparatus 11 and the information obtained by the MRI apparatus 12. The PET-MRI hybrid system 10 is provided with a cradle 13 (on which a subject lies) and a cart 14, which supports the cradle 13 and which is configured to reciprocate between the PET apparatus 11 and the MRI apparatus 12. This is so that the examination of a subject is carried out using a single system. The subject is located at the PET apparatus 11 and the MRI apparatus 12 by the cart 14 and each device carries out its examination. The fusion image of a brain is obtained based on the information obtained from each device.

A circular PET apparatus may be employed as the PET apparatus 11. The examination in the circular PET apparatus 11 can be carried out when the cradle 13 is moved in close proximity of the circular PET apparatus 11 and is then located in place where the examination can be carried out. The MRI apparatus 12 has a magnetic field tube 12a, which generates a magnetic field and carries out the examination, and an examination table 12b. Since the examination in the MRI apparatus 12 is carried out in the magnetic field tube 12a, the MRI apparatus 12 is configured such that the examination table 12b can be moved into and out of the magnetic field tube 12a.

Accordingly, in order to construct the PET-MRI hybrid system comprising the PET apparatus and the MRI apparatus, a novel constitution must be provided, wherein the cradle 13 is moved to the examination table 12b of the MRI apparatus 12 for the examination in the MRI apparatus 12 and the cradle 13 is withdrawn from the examination table 12b of the MRI apparatus 12 after the examination in the MRI apparatus 12. Further, the examination table 12b of the MRI apparatus 12 is moved into and out of the magnetic field tube 12b as explained above. Therefore, there is a problem with a constitution wherein the cradle 13 is simply moved to the examination table 12b in that the cradle 13 cannot be accurately withdrawn from the examination table 12a after the examination in the MRI apparatus 12.

BRIEF DESCRIPTION OF THE DRAWINGS

Arrangements and embodiments may be described in detail with reference to the following drawings in which like reference numerals refer to like elements and wherein.

FIG. 15 is a side view of the cradle transferring device when the shuttle table is lowered after the cradle is locked to the examination table of the MRI apparatus.

DETAILED DESCRIPTION

A detailed description may be provided with reference to the accompanying drawings. Herein, the terms "frontward" and "rearward" are intended to mean a direction away from an examination table of an MRI apparatus and an opposite direction thereof, respectively. One of ordinary skill in the art may realize that the following description is illustrative only and is not in any way limiting. Other embodiments of the present invention may readily suggest themselves to such skilled persons having the benefit of this disclosure.

Figure 1:
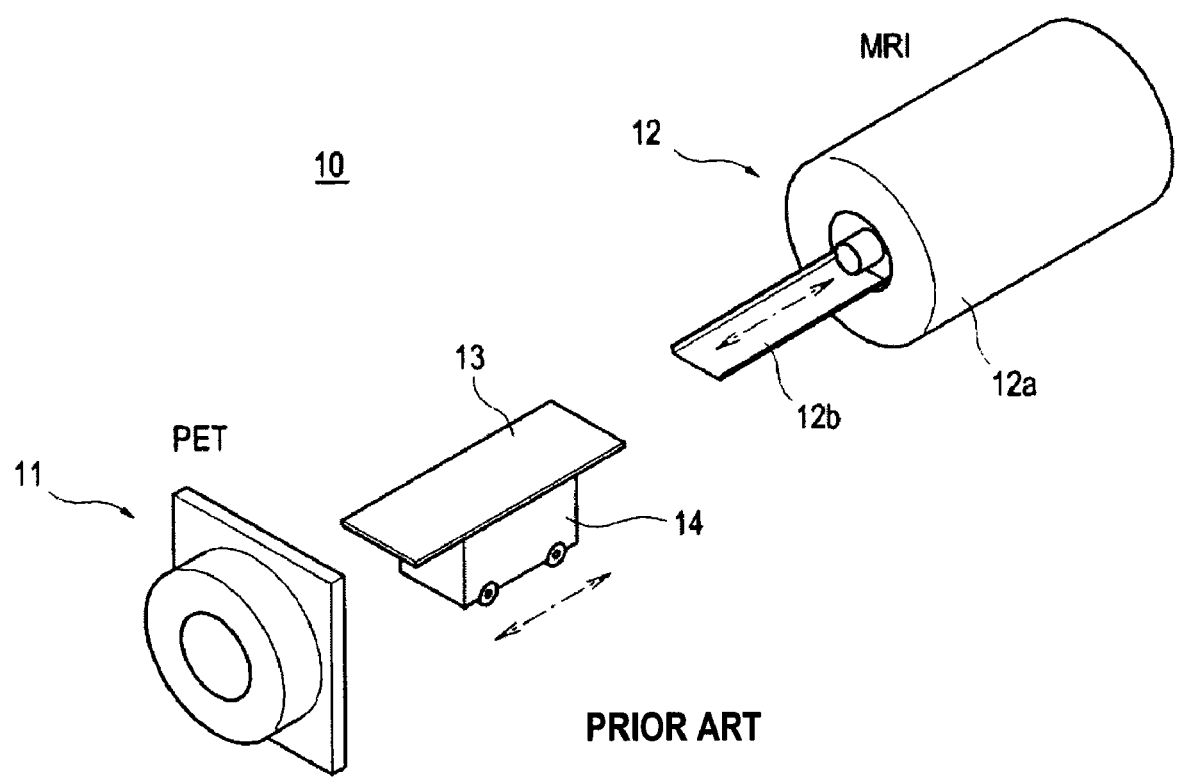
FIG. 1 shows a schematic constitution of a PET-MRI hybrid system.
Figure 2:
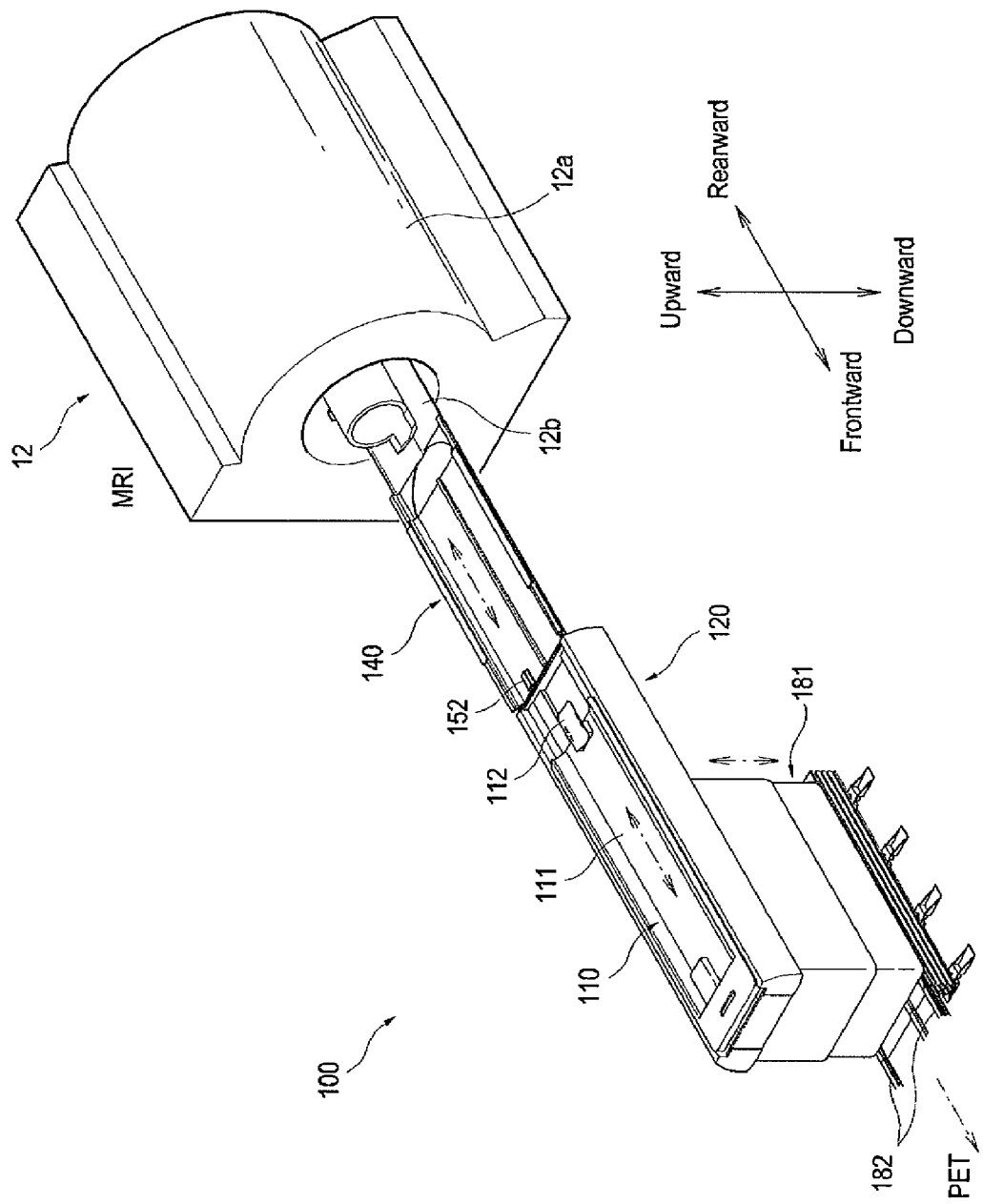
FIG. 2 is a perspective view showing a device for transferring a cradle according to the present invention.

FIG. 2 is a perspective view of a device for transferring a cradle, which is constructed in accordance with one embodiment of the present invention. Referring to FIG. 2, the cradle transferring device 100 comprises the following: a cradle 110 configured such that a subject lies thereon; a shuttle table 120 for moving and withdrawing the cradle 110 to and from an examination table 12b of a medical imaging equipment while supporting the cradle 110; and a cradle receiving member 140 provided on the examination table 12b of the medical imaging equipment for maintaining the cradle 110, which is transferred from the shuttle table 120, on the examination table 12b. The shuttle table 120 includes a transfer member (not shown) and a transfer member driving means (not shown). The transfer member is located in the shuttle table 120 and transfers the cradle 110 as contacted to the cradle 110. The transfer member driving means reciprocates the transfer member along the shuttle table 120.

The medical imaging equipment 12 is configured to examine the diseased part of a subject and obtains images related thereto. Further, the medical imaging equipment 12 is configured so that the examination table 12a can be moved into and out of the part, in which an examination is carried out. In this embodiment, the medical imaging equipment 12 is configured as a MRI apparatus and the examination table is configured to be moved into and out of a magnetic field tube 12a of the MRI apparatus.

The cradle 110 includes a rectangular cradle plate 111. The cradle plate 111 is dimensioned so that a subject can sufficiently lie thereon. At a rear side of the cradle plate 111, a support 112 is provided, on which a head of a subject is placed. The cradle 110 is located on the shuttle table 120 and is moved toward the examination table 12b by the transfer member (not shown).

The shuttle table 120 is mounted on a table cart 181 while supporting a lower side of the cradle 110. The table cart 181 has a component for lifting and lowering the shuttle table 120 and a component for effectuating a self-movement along a rail 182. One end of the rail 182 extends to the vicinity of a front side of the examination table 12b. The other end of the rail 182 extends to an examination part of another medical imaging equipment, which is equipped together with the MRI apparatus 12 in order to obtain fusion images (e.g., a PET apparatus 11).

Thus, the shuttle table 120 is reciprocated between the PET apparatus and the MRI apparatus by the table cart 181. As such, there may be the cradle transferring device for transferring and withdrawing the cradle to and from the examination table of the medical imaging equipment. More specifically, the cradle transferring device 100 may be provided for transferring and withdrawing the cradle 110 to and from the examination table 12b of the MRI apparatus in a PET-MRI hybrid system configured to obtain fusion images by integrating a PET apparatus and a MRI apparatus.

Figure 3:
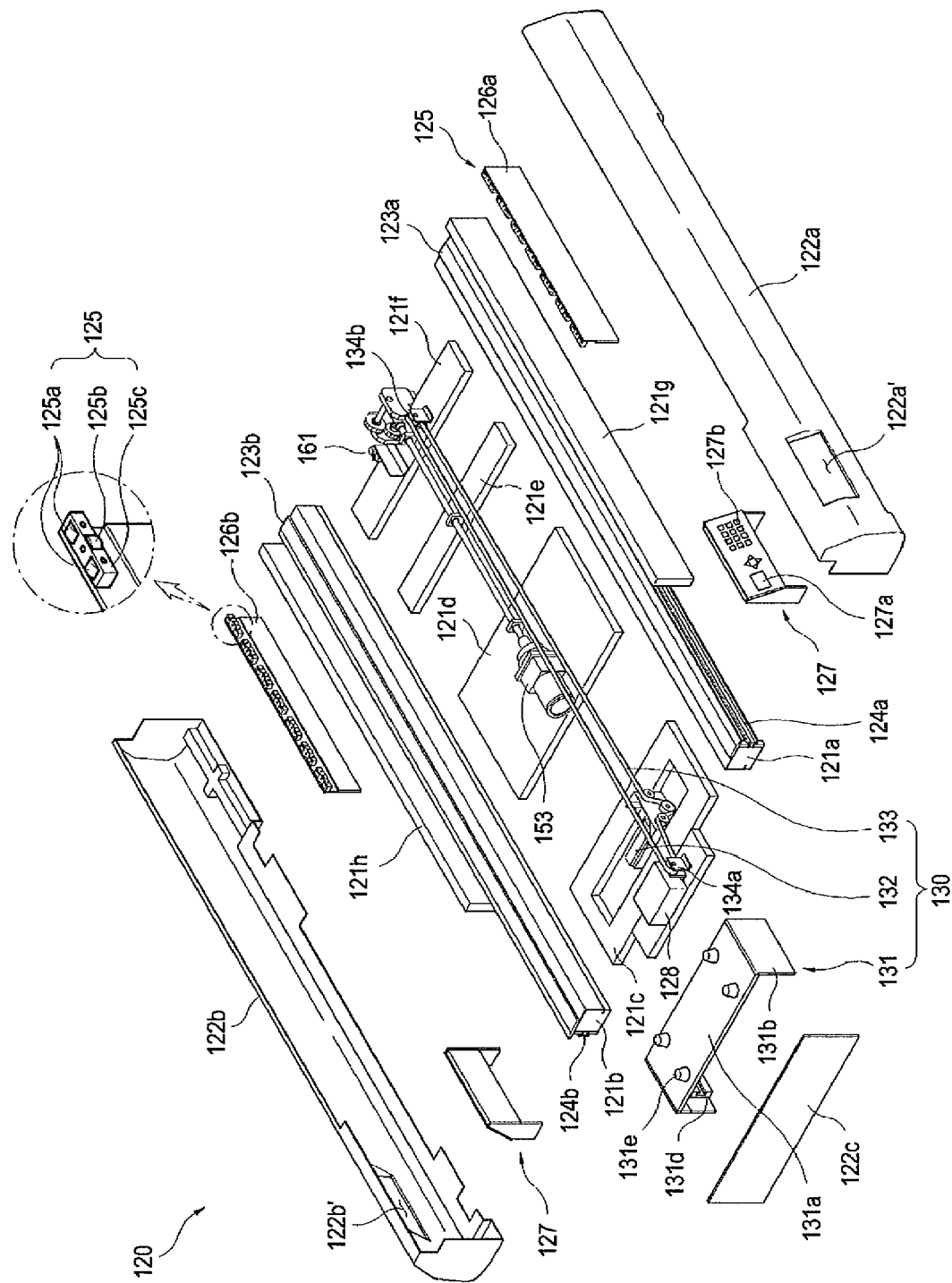
FIG. 3 is a front exploded perspective view of a shuttle table.
Figure 4:
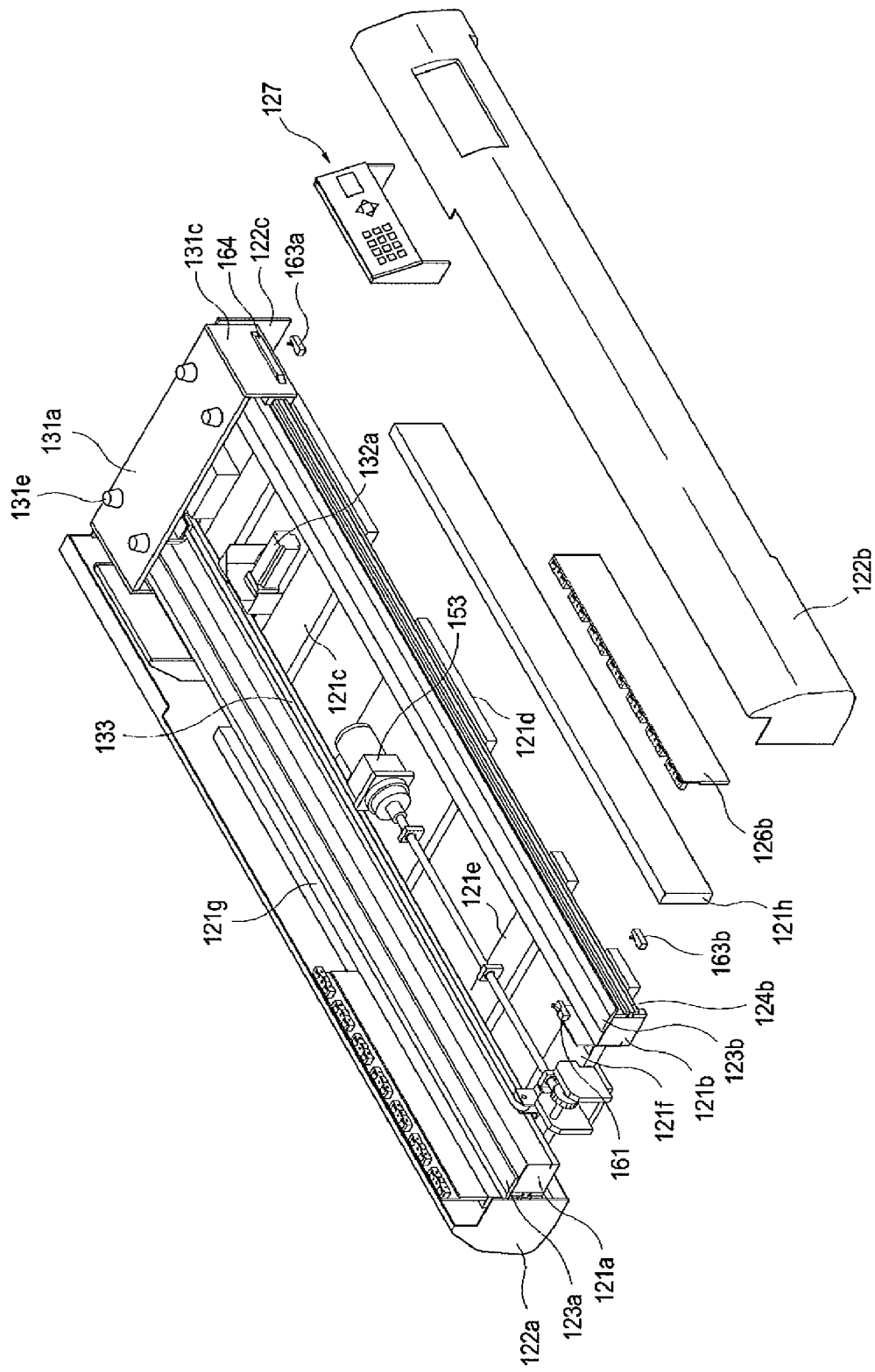
FIG. 4 is a rear exploded perspective view of the shuttle table.

FIG. 3 is a front exploded perspective view of the shuttle table 120. FIG. 4 is a rear exploded perspective view of the shuttle table 120.

Referring to FIGS. 3 and 4, the shuttle table 120 includes: a frame assembly 121a to 121h constituting a framework of the shuttle table 120; and a cover portion 122a to 122c mounted to the frame assembly 121a to 121h and forming an external appearance of the shuttle table 120.

The frame assembly 121a to 121h comprises transfer frames 121a and 121b, a plurality of transverse frames 121c to 121f and side frames 121g and 121h. The transfer frames 121a and 121b are placed in a lengthwise direction of the shuttle table 120 and support a lower side of the cradle 110 along a lengthwise direction of the cradle 110 while serving as a base for the movement of the cradle 110. The transverse frames 121c to 121f are coupled to the transfer frames 121a and 121b and are placed in a widthwise direction of the shuttle table 120. The side frames 121g and 121h are coupled to the transverse frames 121d to 121f as spaced apart from the transfer frame 121a and 121b. The frame assembly 121a to 121h is located such that the frontward end portion of the examination table 12b of the MRI apparatus and the rearward end portion of the transfer frames 121a and 121b are opposed to each other.

The transfer frames 121a and 121b comprise elongated bars or beams. The transfer frames 121a and 121b are provided at both lateral sides of the shuttle table 120 along its lengthwise direction. The cradle 110 is moved in the lengthwise direction of the shuttle table 120 by the transfer member 131 as supported on the transfer frames 121a and 121b.

Roller plates 123a and 123b, with which a cradle roller 115a (see FIG. 7) mounted on the lower side of the cradle 110 is in rolling contact, are provided on the transfer frames 121a and 121b, respectively. Further, guide bars 124a and 124b, which a linear guide 131d (see FIG. 5) of the transfer member 131 is engaged to, are provided on a lateral side of each transfer frame 121a, 121b. The linear guide slides on the guide bar as fitted thereto.

The cover portion 122a to 122c includes: two side covers 122a, 122b coupled to the transverse frames 121c to 121f; and a rear cover 122c coupled to a frontward portion of the side covers 122a, 122b and the frontward portion of the transfer frames 121a, 121b.

The shuttle table 120 further includes a plurality of rolling motion members 125, which limit the upward and downward movements of the cradle and guarantee the movements of the cradle in the lengthwise direction of the shuttle table 120. The rolling motion member 125 includes: a first roller 125a rotatable in the moving direction of the cradle 110; a second roller 125b rotatable in a direction perpendicular to the rotating direction of the first roller 125a; and a bracket 125c rotationably supporting the first roller 125a and the second roller 125b. The rolling motion member 125 is mounted to the side cover 122a, 122b through a fixing plate 126a, 126b.

An input device 127, which a user operates in order to transfer the cradle 110 or to drive the shuttle table 120 or the table cart 181, is provided on the shuttle table 120. The input device 127 includes a display panel 127a and a plurality of keys 127b. The input device 127 is mounted to the shuttle table 120 so that the display panel 127a and the keys 127b are exposed through openings 122a', 122b' formed in the side cover 122a, 122b. The input device 127 is connected to a controller 128, which controls the operations of the cradle transferring device 100. The controller 128 controls a transfer member driving means and a cradle locking means, which will be described later.

A cradle transferring means 130, which moves and withdraws the cradle 100 to and from the examination table 12a, is provided in the shuttle table 120. The cradle transferring means 130 includes: the transfer member 131 engagable to the cradle 110 for transferring the cradle 110; and the transfer member driving means 132, 133 for driving the transfer member 131.

The transfer member 131 is slidably moved along the transfer frames 121a, 121b as supported by the transfer frames 121a, 121b.

Figure 5:
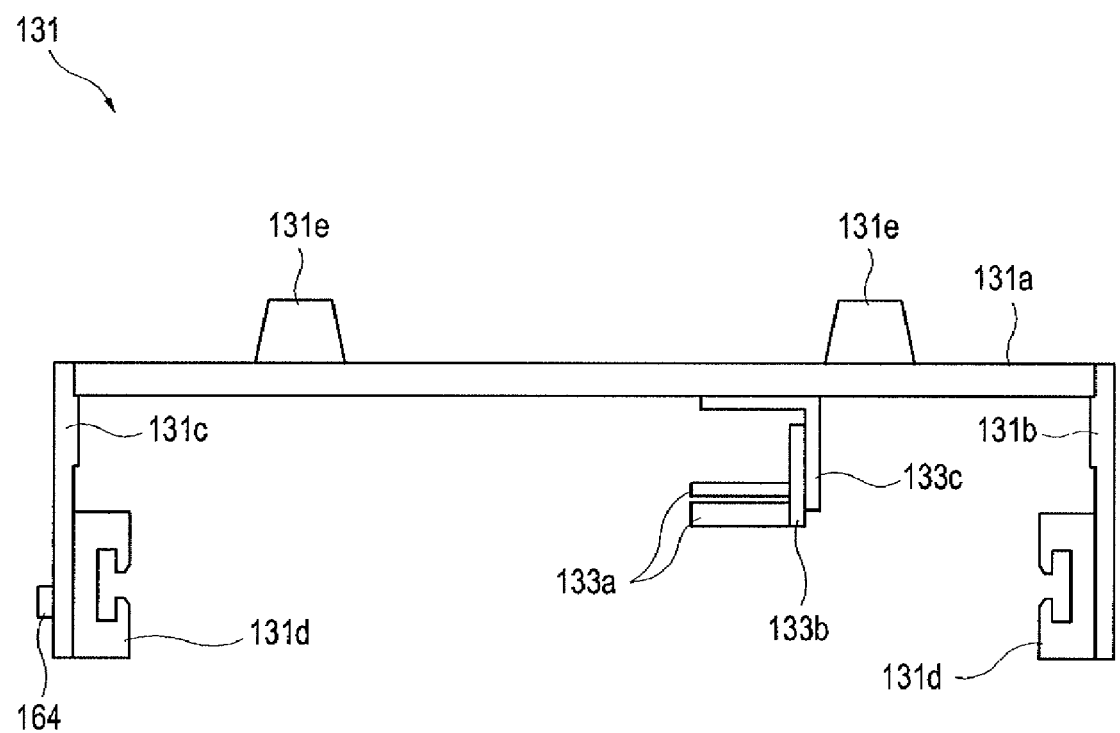
FIG. 5 is a front view of a transfer member.

FIG. 5 is a front view of the transfer member 131. The transfer member 131 includes: a cradle supporting plate 131a configured so as to extend between the transfer frames 121a, 121b; transfer plates 131b, 131c coupled to lateral sides of the cradle supporting plate 131a; and linear guides 131d mounted on an inner surface of the transfer plate 131b, 131c. The linear guide 131d is fitted to the above-mentioned guide bar 124a, 124b. Therefore, the transfer member 131 can be slidably moved along the transfer frame 121a, 121b.

On the upper side of the cradle supporting plate 131a are provided cradle horns 131e as a holder for holding the lower side of the cradle 110. The cradle horns 131e take the form of a cylinder or a truncated cone. The cradle horns 131e are arranged so as to be mated to holder engagement portions 113 (see FIG. 7), which will be described later.

The transfer member driving means 132, 133 includes a motor portion 132 and a timing belt 133 for converting the rotation of the motor portion 132 into the linear movements of the transfer member 131.

Figure 6:
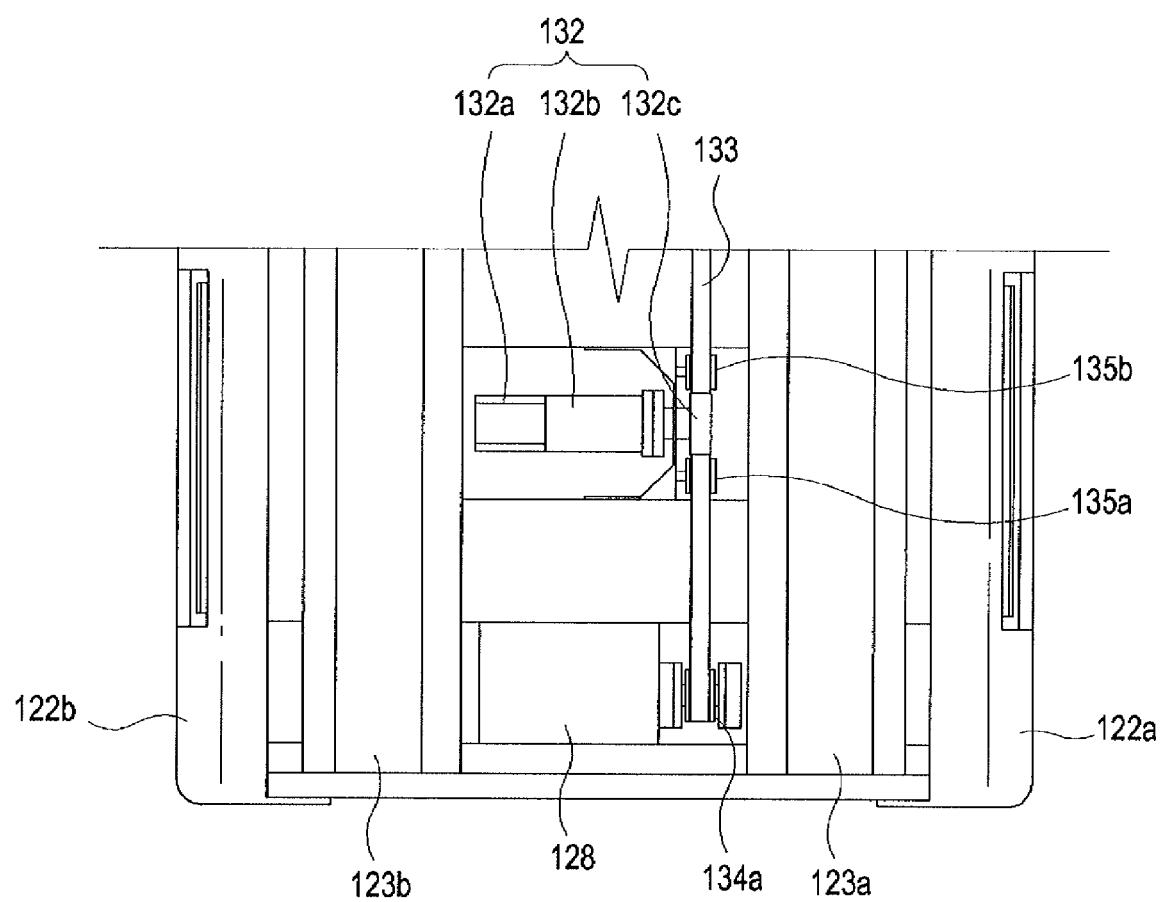
FIG. 6 is a partial plan view of the shuttle table showing drive transfer member driving means.

FIG. 6 is a partial plan view of the shuttle table 120 showing the transfer member driving means 132, 133. Referring to FIG. 6, the motor portion 132 includes: a servomotor 132a producing normal and reverse rotations; a decelerator 132b; and a timing pulley 132c. In the vicinity of the timing pulley 132c is provided idle pulleys 135a, 135b for applying the tension to the timing belt 133.

The timing belt 133 winds along the transfer frames 121a, 121b. One end of the timing belt 133 is joined to the transfer member 131. The other end of the timing belt is joined to the transfer member 131 after passing through the timing pulley 134a (see FIG. 3) provided on the transverse frame 121c, idle pulleys 135a, 135b, timing pulley 132c and the timing pulley 134b (see FIG. 3) provided on the transverse frame 121f. Both ends of the timing belt 133 are secured between a pair of belt securing plates 133a provided on the transfer member 131. The belt securing plate 133a is fixed to the lower side of the cradle supporting plate 131a by belt brackets 133b, 133c (see FIG. 5).

When the servomotor 132a operates, the timing belt 133 is pulled in one direction. Then, the transfer member 131 is slidably moved along the transfer frame 121a, 121b while supported by the transfer frame 121a, 121b. Since the cradle horn 131e of the transfer member 131 is fitted into the holder engagement portion 113 of the cradle 110, the cradle 110 can be also moved along the transfer frames 121a, 121b with the rotation of the servomotor 132a.

Accordingly, the transfer member 131 is reciprocated in the shuttle table 120 between one position (wherein the cradle 110 is fully pushed up to the rearward end portion of the shuttle table 120 and most of the cradle is placed on the examination table 12b of the MRI apparatus and the transfer member 131 cannot be further moved; hereinafter referred to as "a first position") and the other position (wherein the cradle 110 is fully pulled up to the frontward end portion of the shuttle table 120; hereinafter referred to as "a second position").

Figure 7:
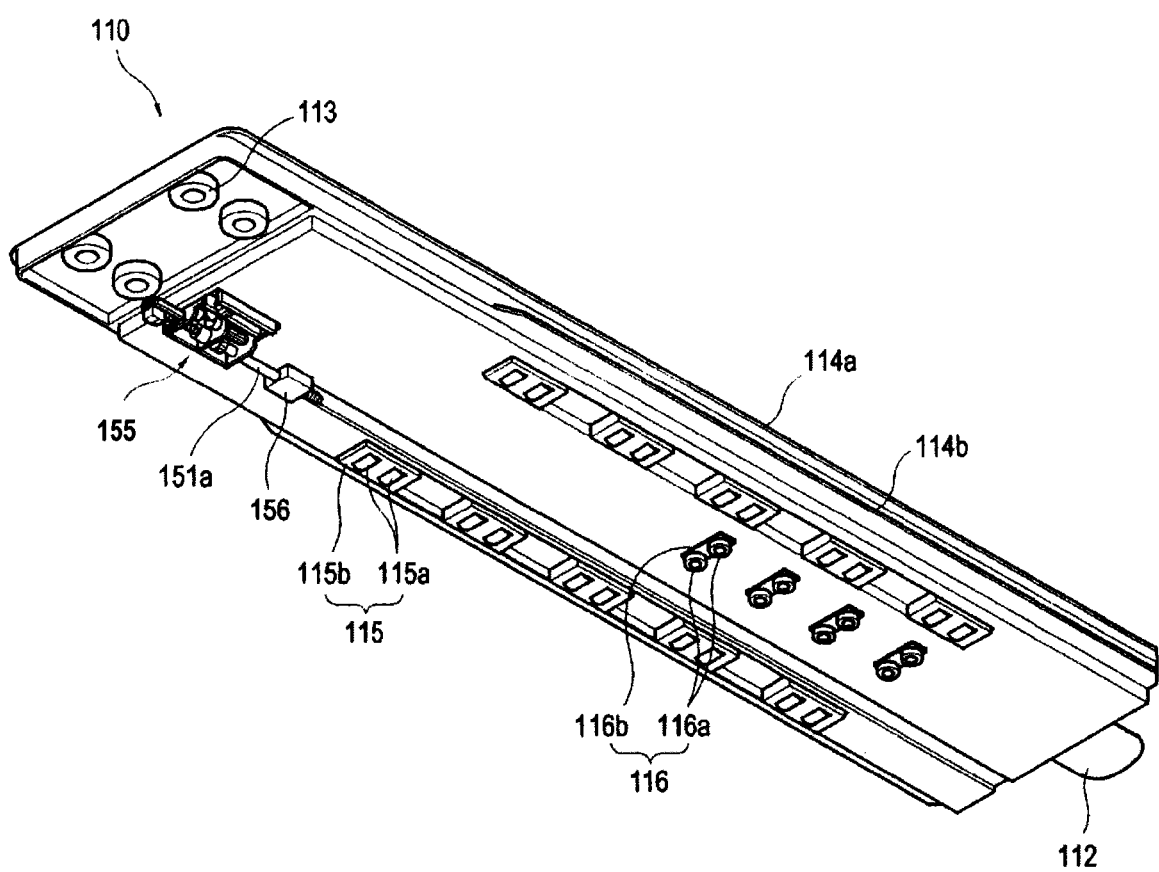
FIG. 7 is a bottom perspective view of a cradle.
Figure 8:
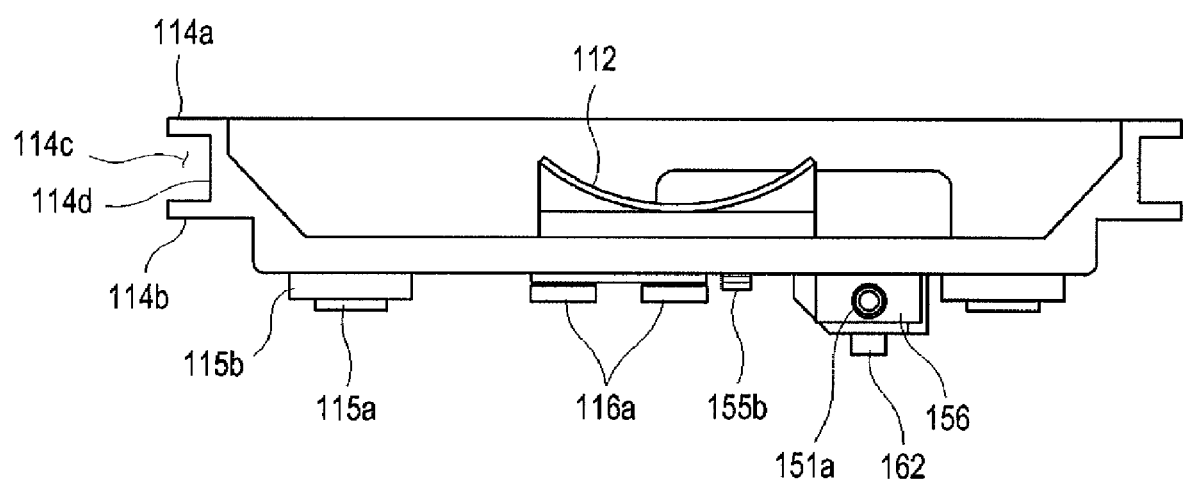
FIG. 8 is a rear view of the cradle.

FIG. 7 is a bottom perspective view of the cradle 110. FIG. 8 is a rear view of the cradle 110.

Referring to FIGS. 7 and 8, the cradle 110 includes the holder engagement portions 113 corresponding to the cradle horns 131e adjacent to the one end of the cradle plate 111. The holder engagement portions are provided so as to correspond to the arrangement and number of the cradle horns. The holder engagement portion 113 is cylinder-shaped so that the cradle horn 131 is fitted thereto. If the cradle horn 131e is fitted to the holder engagement portion 113, then the transfer member 131 hooks the cradle 110. Alternatively, the cradle horn 131e may be provided on the lower side of the cradle and the holder engagement portion 113 may be provided on the upper side of the transfer member 131.

Guide portions 114a to 114c, to which the rolling motion member 125 of the shuttle table 120 is fitted, are formed along both lateral sides of the cradle plate 111. The guide portion 114a to 114c includes a first protrusion 114a formed elongatedly along the lateral side of the cradle plate 111 and a second protrusion 114b formed elongatedly along the lateral side of the cradle plate 111 and parallel to the first protrusion 114a. Therefore, a groove 114c of constant width is defined between the first protrusion 114a and the second protrusion 114b. The rolling motion member 125 contacts the groove 114c. More specifically, the first roller 125a of the rolling motion member 125 is brought into contact with a lower surface of the first protrusion 114a or an upper surface of the second protrusion 114b. Further, the second roller 125b is brought into contact with a wall portion 114d of the guide portion. Therefore, the upward or downward movement of the cradle 110 relative to the shuttle table 120 is limited by the first roller 125a and the lower surface of the first protrusion 114a or the upper surface of the second protrusion 114b. The widthwise movement of the cradle 110 relative to the shuttle table 120 is limited by the second roller 125b and the wall portion 114d of the guide portion 114.

On the lower side of the cradle plate 111 is provided a cradle roller portion 115, which is brought into rolling contact with the roller plate 123a, 123b provided on the transfer frame 121a, 121b. The cradle roller portion 115 has a cradle roller 115a and a bracket 115b. The cradle roller 115a is disposed on the lower side of the cradle plate 111 in a lengthwise direction of the roller plate 123a, 123b. The cradle roller 115a is rotatably mounted to the lower side of the cradle plate 111 by the bracket 115b.

Further, on the lower side of the cradle plate 111 are provided a plurality of rolling members 116 as a first guide member, which allows the cradle 110 to be moved to the examination table 12b in an orientation, wherein the cradle 110 is situated on the shuttle table 120 and which does not allow the cradle 110 to be moved on the examination table 12b in a widthwise direction of the examination table 12b. The rolling member 116 includes: a pair of guide rollers 116a rotatable in the moving direction of the cradle 110; and a fixing plate 116b for fixing the guide rollers 116a to the cradle plate 111. A gap between the guide rollers 116a is set such that a guide bar (see FIG. 9) embodying a second guide member 142 is fitted between the guide rollers 116a.

Figure 9:
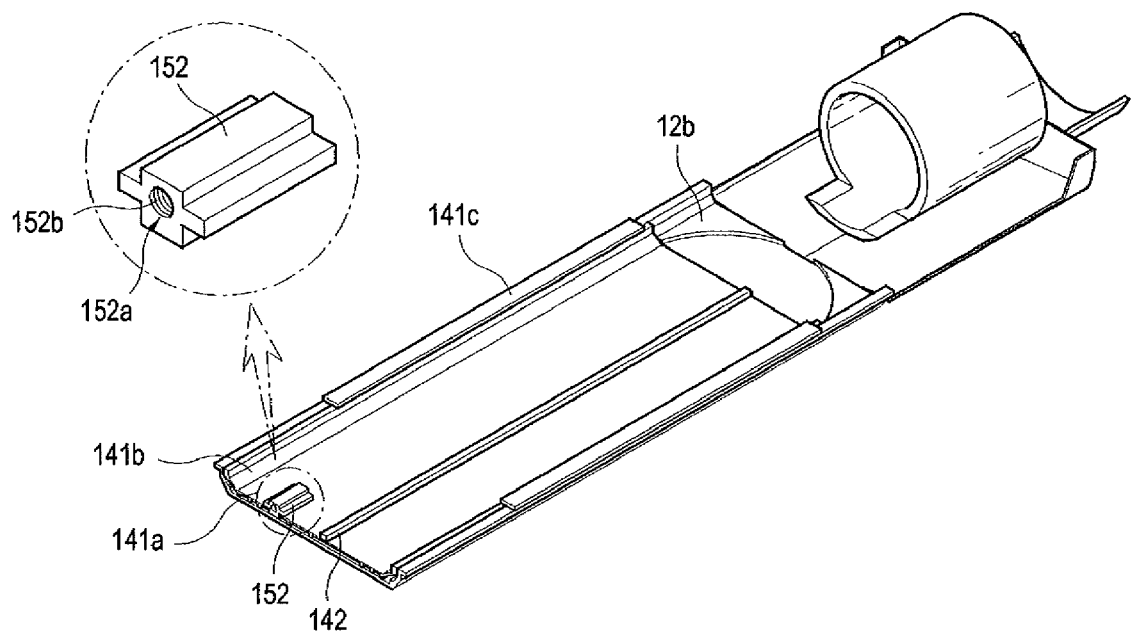
FIG. 9 is a perspective view of an examination table of a MRI apparatus showing a cradle receiving member.
Figure 10:
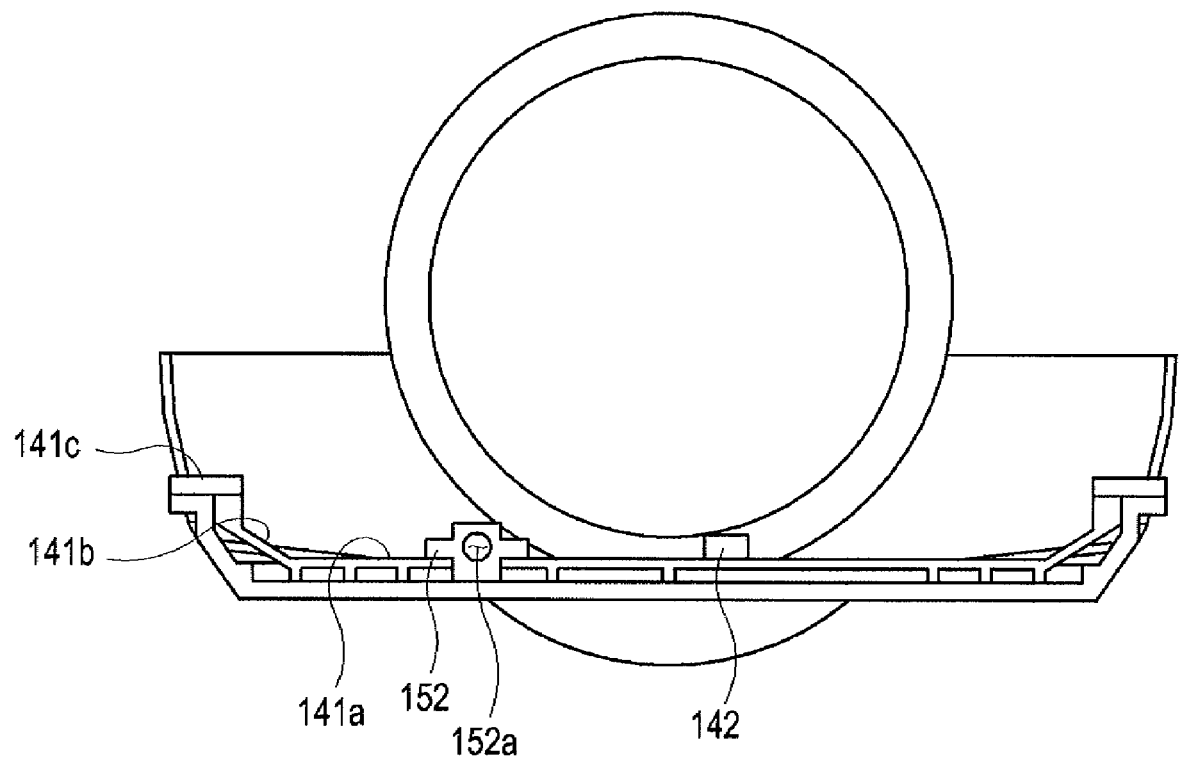
FIG. 10 is a front view of the examination table of the MRI apparatus showing a cradle receiving member.

FIG. 9 is a perspective view of the examination table 12b of the MRI apparatus. FIG. 10 is a front view of the examination table of the MRI apparatus.

Referring now to FIGS. 9 and 10, the cradle receiving member 140, which is located on the examination table 12b of the MRI apparatus, includes: a supporting member 141a, 141b located on the examination table 12b for supporting the lower side of the cradle 110; and a second guide member 142, with which the rolling member 116 is brought into rolling contact.

The supporting member 141a, 141b has a rectangular plate-like portion 141a and fixing portions 141b formed at both lateral sides of the plate-like portion 141a. The plate-like portion 141a has a length sufficient to receive the cradle 110. When the cradle 110 is moved from the shuttle table 120 to the cradle receiving member 140, the cradle roller 115a is brought into rolling contact with an upper side of the plate-like portion 141a. The front end portion of the plate-like portion 141a is positioned to be aligned with the front end portion of the examination table 12b. The fixing portion 141b of the plate-like portion 141a is fixed to a side edge of the examination table 12b by a fixture 141c so that the supporting member 141 is secured on the examination table 12b.

A guide bar 142, which constitutes the second guide member corresponding to the first guide member 116, is provided on the plate-like portion 141a. The guide bar 142 has a length corresponding to the length of the plate-like portion 141a. The guide bar 142 is oriented on the plate-like portion 141a to be parallel to the transferring direction of the cradle 110. The width of the guide bar 142 equals the above-described gap between the guide rollers 116a. The guide bar 142 is disposed on the plate-like portion 141a such that the guide bar 142 can be located between the guide rollers 116a when the cradle 110 is moved to the examination table 141a. Alternatively, the guide rollers 116a may be disposed on the plate-like portion 141a in its lengthwise direction and the guide bar 142 may be disposed on the lower side of the cradle plate 111.

The movement of the cradle 110 to the examination table 12b will be now described with reference to FIGS. 2 to 10.

When the upper surface of the transfer frames 121a, 121b and the upper surface of the plate-like portion 141a are at the same level and the cradle 110 is situated in the second position, the table cart 181 travels to the vicinity of the front portion of the examination table 12b of the MRI apparatus along the rail 182. The table cart 181 stops when the rearward end portion of the transfer frames 121a, 121b and the frontward end portion of the plate-like portion 141a is positioned to be slightly apart from each other. In such a state, if the servomotor 132a rotates in the direction wherein the cradle 110 is moved to the examination table 12b, then the transfer member 131 is moved toward the examination table 12b by the timing belt 133. At the same time, the cradle 110 is moved to the examination table 12b. The cradle 110 can be moved only in the lengthwise direction of the shuttle table 120 due to the guide portion 114a to 114c and the rolling motion member 125. Further, since the cradle roller 115a is brought into rolling contact with the roller plate 123a, 123b and the plate-like portion 141a, the cradle 110 can be moved to the examination table 12b softly and smoothly.

Since the guide bar 142 is fitted between the pair of guide rollers 116a during transferring the cradle 110 to the examination table 12b, the cradle 110 is positioned on the examination table 12b in the same orientation as its orientation in the shuttle table 120. Therefore, when the cradle 110 is transferred from the examination table 12b to the shuttle table 120 after the examination in the MRI apparatus, the orientation of the cradle is not changed.

The cradle transferring device 100 further comprises cradle locking means for locking the cradle 110 to the examination table 12b. This is so that the cradle transferred to the examination table 12b is not displaced due to the movement of the examination table 12b.

The cradle locking means comprises the following: a first locking member 151 mounted to the cradle 110 so as to be lengthwisely moved; a second locking member 152 mounted to the examination table 12b for being engaged to and released from the first locking member 151; locking member driving means 153 for driving the first locking member 151; a transmission member 154, 155 for transmitting the operations of the locking member driving means 153 to the first locking member 151; and a position limiting member 156 for limiting the position of the first locking member 151. The transmission member 154, 155 is composed of a first transmission member 154 disposed at the shuttle table 120 and a second transmission member 155 disposed at the cradle 110.

Figure 11:
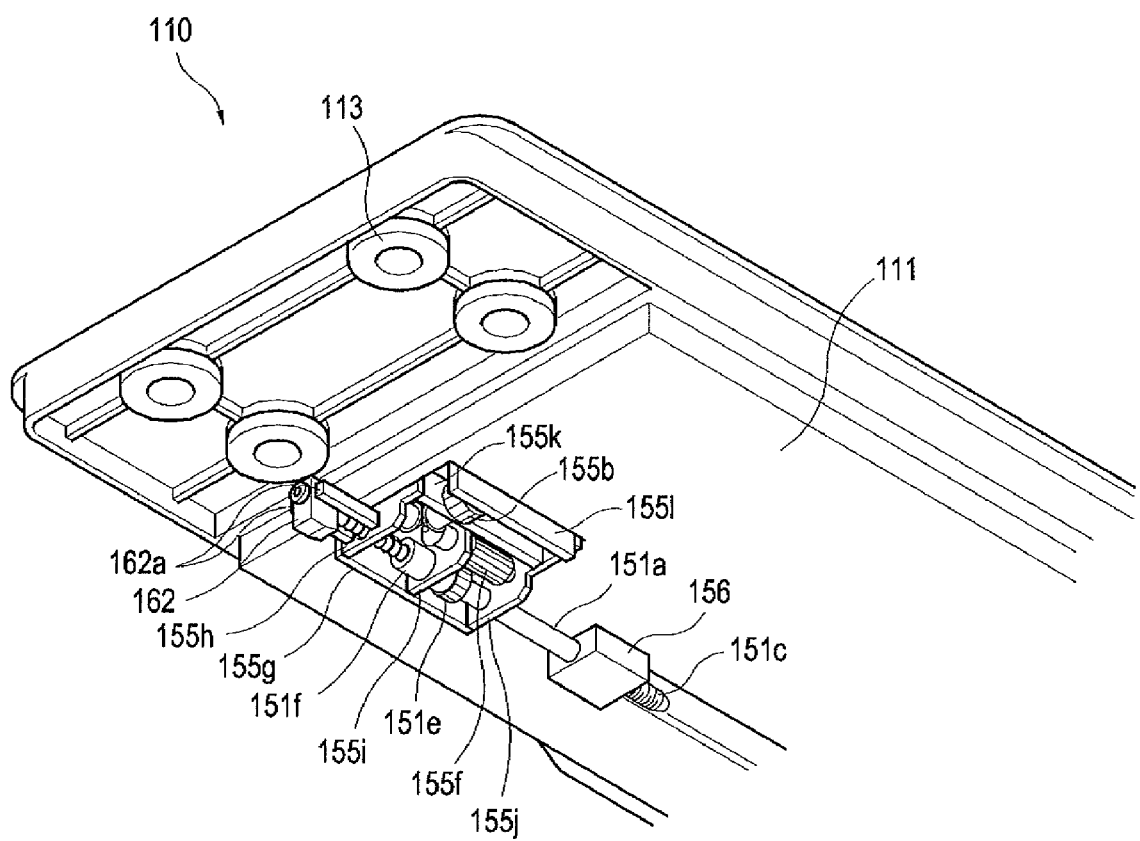
FIG. 11 is a partial perspective view showing a portion of a cradle locking means.
Figure 12:
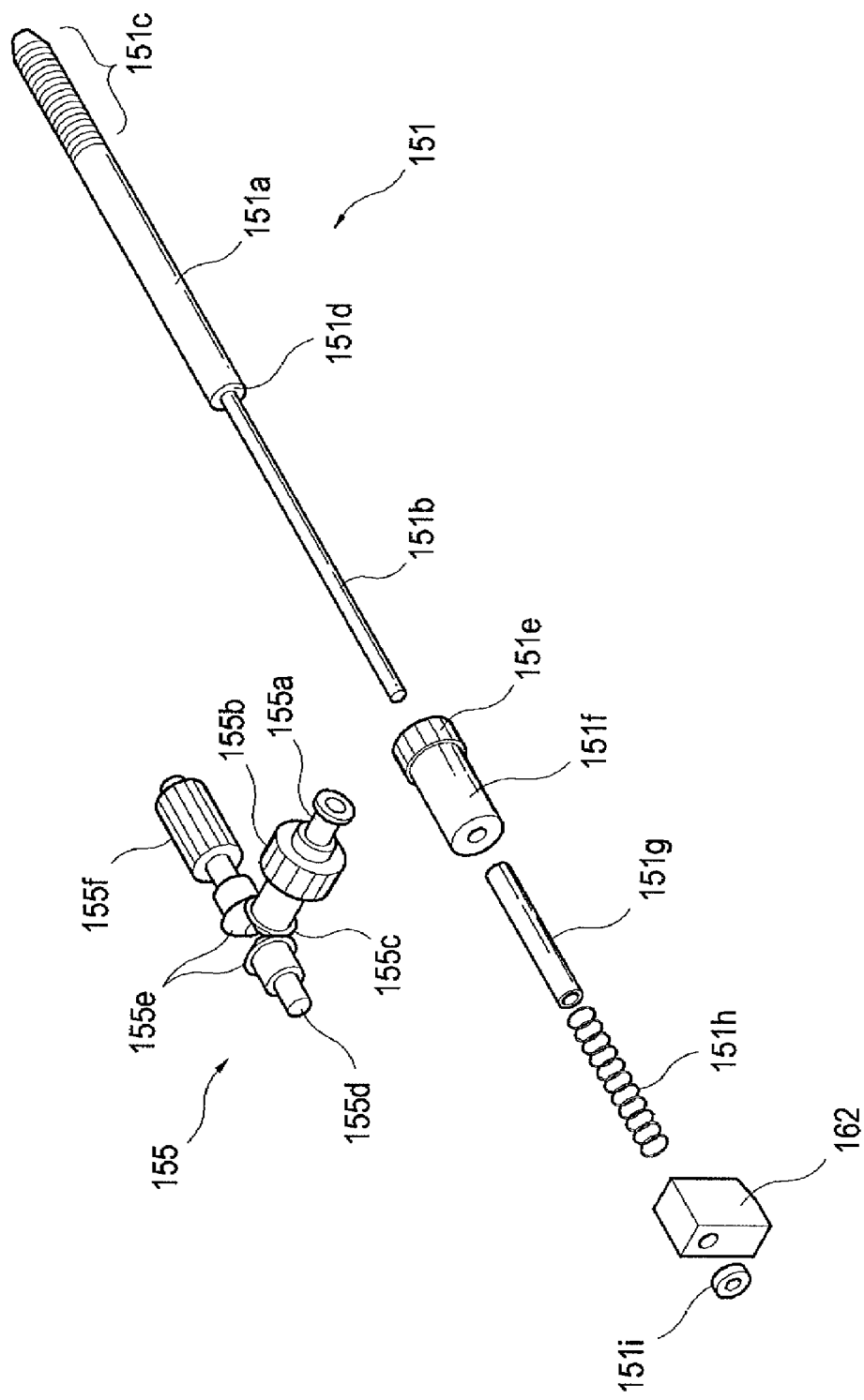
FIG. 12 is an exploded perspective view of the cradle locking means showing a first locking member and a second transmission member.
Figure 13:
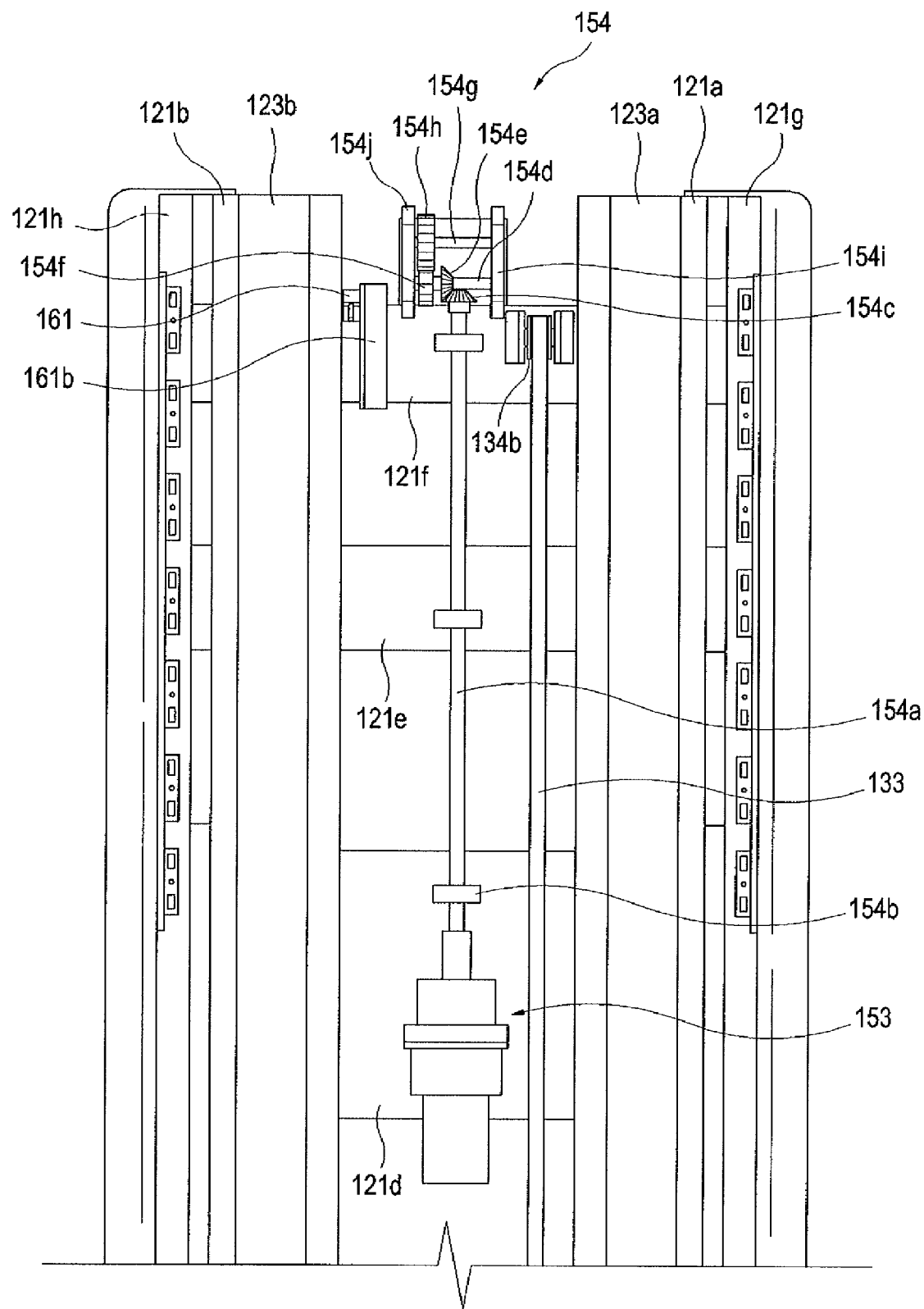
FIG. 13 is a partially enlarged plan view of the shuttle table showing driving means of the first locking member and a first transmission member.

FIG. 11 is a perspective view of a portion of the cradle 110 showing a portion of the cradle locking means. FIG. 12 is an exploded perspective view of the cradle locking means showing the first locking member 151 and the second transmission member 155. FIG. 13 is a partially enlarged plan view of the shuttle table 120 showing the locking member driving means 153 and the first transmission member 154. Each element of the cradle locking means will be now described with reference to FIGS. 9 to 13.

The first locking member 151 includes a shaft 151a, 151b. The shaft 151a, 151b has a first shaft portion 151a formed with a male thread 151c at its rearward end portion and a second shaft portion coupled to the other end of the first shaft portion 151a and having a smaller diameter than that of the first shaft portion 151a. Therefore, a shoulder portion 151d is formed at a joint of the first shaft portion 151a and the second shaft portion 151b. The first locking member 151 further includes a first sleeve 151f and a second sleeve 151g, which are fitted to the second shaft portion 151b. The first sleeve 151f is integrally formed with a spur gear 151e. The first sleeve 151f is secured to the second shaft portion 151b by a key groove (not shown) formed on the second shaft portion 151b and a key (not shown) to be fitted thereto. A switch block 162 is rotatably mounted to the other end of the second shaft portion 151b. The switch block 162 is positioned by fastening a bolt (not shown) through a washer 151i to the other end of the second shaft portion 151b. The functions of the switch block 162 will be described later in detail. The first locking member 151 further includes a compression spring 151h disposed between the switch block 162 and the first sleeve 151f while surrounding the second sleeve 151g. The compression spring 151h limits the position of the first sleeve 151f and the position of the switch block 162. Therefore, due to a resilient force of the compression spring 151h, the first sleeve 151f and the spur gear 151e are pressed against the shoulder 151 and the switch block 162 is pressed against the washer 151i.

The second locking member 152 is disposed at the frontward end portion of the plate-like portion 141a. (see FIG. 9) The second locking member 152 takes the form of an elongated block. The second locking member 152 has a bore 152a, into which the rearward end portion of the first shaft portion 151a is inserted, and a female thread 152b that is formed on a surface of the bore 12 and corresponds to the male thread 151c. The second locking member 152 may be a nut, to which the end portion of the first shaft portion 151a having the male thread 151c is screwed. The second locking member 152 is positioned on the plate-like portion 141a so that the rearward end portion of the shaft 151a, 151b can be inserted into the second locking member 152 when the cradle 110 is transferred to the examination table 12b.

The locking member driving means 153 is mounted on the transverse frame 121d of the shuttle table 120. The locking member driving means 153 includes an induction motor, which produces normal and reverse rotations. The induction motor 153 is controlled by the controller 128 (see FIG. 3).

The rotation of the induction motor 153 is transmitted through the first transmission member 154 toward the rearward end portion of the shuttle table 120. The first transmission member 154 includes a transmission shaft 154a, a pair of bevel gears 154c, 154e and a pair of spur gears 154f, 154h. The transmission shaft 154a is coupled to a rotating shaft of the induction motor 153 at its one end and is supported on the transverse frame 121d, 121e, 121f by supporters 154b. The bevel gear 154c is fixed to the other end of the transmission shaft 154a and is engaged to the bevel gear 154e. The bevel gear 154e is rotated together with the spur gear 154f. The spur gear 154f is engaged to the spur gear 154h. The bevel gear 154e and the spur gear 154f are rotatably joined to a bracket 154i through a shaft 154d and the spur gear 154h is rotatably joined to a bracket 154j through a shaft 154g. The brackets 154i, 154j are mounted on the transverse frame 121f.

The normal rotation or reverse rotation caused by the induction motor 153 is effectuated as a clockwise or counterclockwise rotation of the spur gear 154h through the pair of bevel gears 154c, 154e and the spur gear 154f. The rotation of the spur gear 154h is transmitted to a spur gear 155b of the second transmission member 155. The spur gear 154h and the spur gear 155b are arranged in line parallel to the lengthwise direction of the transfer frames 121a, 121b. The second transmission member 155 is positioned on the lower side of the cradle plate 111 such that the spur gear 154h and the spur gear 155b are engaged to each other when the transfer member 131 is situated at the first position.

The second transmission member 155 is mounted at the front portion of the cradle (more specifically, at the front lower side of the cradle plate 111). The first locking member 151 is rotatably and movably disposed at the second transmission member 155.

The second transmission member 155 includes the spur gear 155b, a pair of bevel gears 155c, 155e and a spur gear 155f. The spur gear 155b is fixed in the middle of a rotating shaft 155a and the bevel gear 155c is fixed to one end of the rotating shaft 155a. The rotating shaft 155a is rotatably joined to brackets 155k, 155l, which are mounted on the lower side of the cradle plate 111. The bevel gear 155c is engaged to the bevel gear 155e, which is fixed to a rotating shaft 155d. The spur gear 155f is fixed to the other side of the rotating shaft 155d. The rotating shaft 155d is rotatably joined to brackets 155h, 155i, 155j, which are mounted together with a bracket 155g on the lower side of the cradle plate 111. Accordingly, the rotation of the spur gear 155b is effectuated as the spur gear 155f rotates through the pair of bevel gears 155c, 155e.

The first shaft portion 151a and the first sleeve 151f are rotatably mounted as passing through the brackets 155i, 155j, respectively, so that the spur gear 151e is engaged to the spur gear 155f. Therefore, the rotation of the spur gear 155f is effectuated as the first locking member 151 rotates through the spur gear 151e. Consequently, when the spur gear 154h and the spur gear 155b are engaged to each other, the normal rotation or reverse rotation of the induction motor 153 is effectuated as the first locking member 151 rotates clockwise or counter-clockwise.

The position limiting member 156 is located on the lower side of the cradle plate 111 apart from the second transmission member 155 toward the rearward of the cradle 110. The position limiting member 156 takes the form of a hexahedral block. The position limiting member 156 has a bore 156a, through which the first shaft portion 151a passes. Preferably, the bore 156a is formed with a female thread 156b corresponding to the male thread 151c. The rearward end portion of the first shaft portion 151a passes through the position limiting member 156 while being screwed thereto. The position limiting member 156 is positioned such that the center of the bore 156a is aligned in line with a center of the bore 152a of the second locking member 152 in the moving direction of the cradle 110. Since the position limiting member 156 and the first shaft portion 151a are screw-engaged to each other, the first locking member 151 does not slip while transferring the cradle 110. Further, the position limiting member 156 supports the first locking member 151 when the first locking member 151 and the second locking member 152 are engaged to each other in order to lock the cradle 110.

Since the first transmission member 154 is disposed at the rearward side of the shuttle table 120 and the second transmission member 155 is disposed at the frontward side of the cradle 110, connection and disconnection can occur between the induction motor 153 and the first locking member 151. Thus, when the frontward of the cradle 110 is located on the rearward of the shuttle table 120 (e.g., the first position) (more specifically, when the spur gear 155b of the second transmission member is engaged to the spur gear 154h of the first transmission member after the cradle 110 is moved), the connection between the induction motor 153 and the first locking member 151 occurs.

Figure 14:
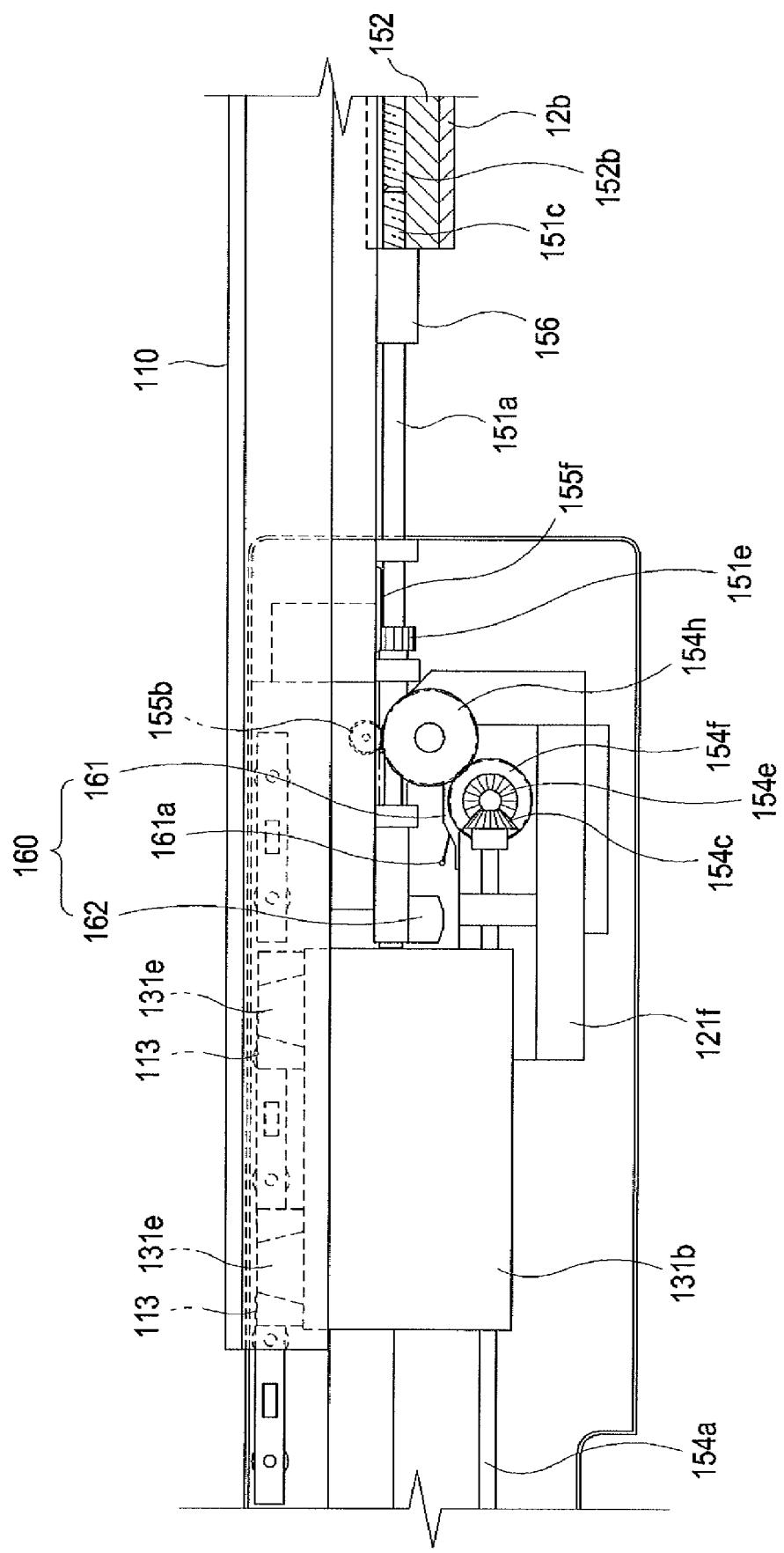
FIG. 14 is a side view of the cradle transferring device when the cradle is transferred to the examination table of the MRI apparatus.

FIG. 14 is a partial side view of the cradle transferring device 100 showing the cradle 100 moved to the examination table 12b of the MRI apparatus.

When the position limiting member 156 is close to the second locking member 152 and the frontward end portion of the first shaft portion 151a is slightly inserted into the bore 152a of the second locking member 152, the movement of the cradle 110 to the examination table 12b of the MRI apparatus ends. At this time, the connection between the first locking member 151 and the induction motor 153 occurs, while the spur gear 154h and the spur gear 155b are engaged to each other. Therefore, the rotating operation of the induction motor 153 can be effectuated as the rotation of the first locking member 151. The frontward end portion of the first shaft portion 151a is screw-engaged to the second locking member 152 by the rotation of the induction motor 153, wherein the cradle 110 is locked to the examination table 12b of the MRI apparatus.

The cradle transferring device 100 further comprises signal generating means 160 for generating a signal controlling the operations of the cradle locking means. The signal generating means generates a first signal for stopping the operation of the induction motor 153 and a second signal for starting the operation of the induction motor 153.

The signal generating means includes a limit switch 161 and the switch block 162 configured to be placed into contact with the limit switch 161.

The limit switch 161 is disposed adjacent to the first transmission member 154 and is mounted to the transverse frame 121f by means of a bracket 161b (see FIG. 13). Preferably, the limit switch 161 has a lever 161a, which is resiliently movable. The limit switch 161 is configured so as to generate signals for stopping or starting the operation of the induction motor 153 when the lever 161a is operated by the switch block 162. The limit switch 161 is connected to the controller 128 and transmits the generated signal to the controller 128.

The switch block 162 is rotatably mounted to the other end of the second shaft portion 151b of the first locking member as described above (see FIGS. 11 and 12). Further, the switch block 162 is sandwiched between a pair of fixing pieces 162a mounted to the bracket 155h. Therefore, when the first locking member 151 is rotated and the first shaft portion 151a advances while being engaged to the second locking block 152, the switch block 162 is moved without rotation as following the advancement of the shaft portion 151a, 151b. When the lever 161a is turned downward in FIG. 14 by the switch block 162 as the first locking member 151 advances to some extent, the limit switch 161 generates the first signal. The limit switch 161a is positioned such that the lever 161a is operated when the first shaft portion 151a is inserted into the second locking member 152 by a sufficient depth. The first signal generated from the limit switch 161 is transmitted to the controller 128 and the controller 128 stops the induction motor 153.

FIG. 15 is a partial side view of the cradle transferring device 153 showing the state where the shuttle table 120 is lowered after the cradle 110 is locked to the examination table 12b of the MRI apparatus.

After the cradle 110 is fully moved to the examination table 12b of the MRI apparatus and is then locked thereto, the shuttle table 120 is lowered by the table cart 14. At this time, as shown in FIG. 15, the first shaft portion 151a of the first locking member is fully screw-engaged to the second locking member 152 and the lever 161a of the limit switch occupies its initial position.

Thereafter, the examination table 12b of the MRI apparatus is moved into the magnetic field tube 12a (see FIG. 2) with the cradle 110 received therein and the examination of MRI apparatus is then performed. After the examination of MRI apparatus is completed, the examination table 12 is moved to its initial position where the cradle 110 is moved thereto as shown in FIG. 15. In such a case, the cradle 110 is not displaced on the examination table 12b of the MRI apparatus by the cradle locking means.

In case the shuttle table 120 is lifted again, since the cradle 110 stays at a location before the examination table 12b of the MRI apparatus is moved, the cradle horns 131e can be mated with the holder engagement portions 113. Accordingly, the cradle 110 can be accurately withdrawn from the examination table 12b of the MRI apparatus to the shuttle table 120. The shuttle table 120 is lifted so that the roller plates 123a, 123b and the plate-like portion 141a are at the same level.

Further, if the shuttle table 120 is lifted, the spur gear 154h and the spur gear 155b are engaged to each other and the connection between the first locking member 151 and the induction motor 154 occurs. At the same time, the switch block 162 turns the lever 161a of the limit switch 161 downward in FIG. 15 and the limit switch 161 generates the second signal thereby. Then, the induction motor 153 is rotated contrary to the case of engaging the first locking member 151 and the second locking member 152. Thus, the first locking member 151 is released from the second locking member 152. After the induction motor 153 is operated until the first locking member 151 is completely released from the second locking member 152, the induction motor 153 is stopped. Thereafter, the cradle 110 is moved to the second position with the operation of the servomotor 132a, thereby completing the withdrawal of the cradle 110 from the examination table 12b of the MRI apparatus.

The signal generating means further includes: limit switches 163a, 163b (see FIG. 4) for generating signals for stopping the operation of the servomotor 132a relating to transferring the cradle 110; and a switch block 164 configured to be placed into contact with the limit switches 163a, 163b. The limit switches 163a, 163b are connected to the controller 128. The switch block 164 is mounted on the transfer plate 131c of the transfer member 131.

The limit switch 163a is positioned in the shuttle table 120 such that it contacts the switch block 164 when the transfer member 131 is located at the second position. The limit switch 163b is positioned in the shuttle table 120 such that it contacts the switch block 164 when the transfer member 131 is located at the first position and the position limiting member 156 is close to the second locking member 152. Thus, if the transfer member 131 reaches the second position, then the servomotor 132a is stopped by the operation of the limit switch 163a. Further, if the transfer member 131 reaches the first position, then the servomotor 132 is stopped by the operation of the limit switch 163b.

Embodiments of the present invention may provide a device for transferring a cradle for use with a medical imaging equipment. The cradle transferring device can move the cradle to the examination table of the medical imaging equipment and can withdraw the cradle from the examination table after the examination of the medical imaging equipment is completed. Since the cradle and the examination table are provided with the guide members, the cradle is situated on the examination table in the same orientation as its orientation in the shuttle table. Since the cradle and the shuttle table supporting it are separated from each other, the movement of the examination table is not obstructed. Since the cradle can be locked to the examination table, the orientation and the position of the cradle are not changed during or after the examination. Thus, the cradle can be accurately withdrawn from the examination table to the shuttle table. Since the cradle transferring device is configured to move and withdraw the cradle to and from the examination table of the MRI apparatus, a PET-MRI hybrid system, which obtains a fusion image by alternately placing a subject at an MRI apparatus and a PET, is realized.

A device for transferring a cradle for use with a medical imaging equipment may be provided. The cradle transferring device may comprise a cradle having a first guide member lengthwisely disposed on a lower side thereof, wherein a subject lies on an upper side thereof. Such a device may also comprise a shuttle table including: a transfer frame for supporting the lower side of the cradle; a transfer member for transferring the cradle, wherein the transfer member is coupled to the transfer frame so as to be movable along the transfer frame; a transfer member driving means for reciprocating the transfer member between a first position (where the transfer member is situated at one end of the transfer frame) and a second position (where the transfer member is situated at the other end of the transfer frame), wherein the shuttle table is positioned so that one end of an examination table of the medical imaging equipment and the other end of the transfer frame are opposed to each other; and a cradle receiving member located on the examination table of the medical imaging equipment for supporting the cradle transferred from the shuttle table, wherein the cradle receiving member has a second guide member lengthwisely disposed on an upper side thereof, wherein the second guide member is configured to contact the first guide member.

One of the first and second guide members may include a plurality of rolling members, while the other may include a guide bar for contacting the rolling members.

The transfer member may have a holder for holding the cradle. Further, the cradle may have a holder engagement portion to which the holder is engaged.

The transfer member driving means may include: a first motor mounted to the shuttle table and producing normal and reverse rotations; and a belt winding along the transfer frame, wherein the belt is driven by the first motor and joined to the transfer member.

The cradle transferring device may further include a cradle locking means. The cradle locking means may include: a first locking member movably mounted to the cradle; and a second locking member fixed to the cradle receiving member, wherein the first locking member is engaged and released to and from the second locking member.

The first locking member may comprise a shaft formed with a male thread at one end thereof. Further, the second locking member may include a nut formed with a female thread therein.

The cradle locking means may further include: a second motor mounted to the shuttle table and producing normal and reverse rotation; and a transmission member for transmitting the rotation of the second motor to the first locking member. The transmission member may comprise a first transmission member disposed on the shuttle table in close proximity of one end of the shuttle table and a second transmission member disposed on the lower side of the cradle as joined together with the first locking member. When the transfer member is situated at the second position, the first transmission member and the second transmission member may be connected to each other and the rotation of the second motor may be transmitted to the rotation of the first locking member.

The cradle transferring device may further comprise signal generating means for generating a first signal for stopping the second motor and a second signal for actuating the second motor.

The signal generating means may include a switch block disposed at the first locking member and a limit switch disposed at the one end of the transfer frame. The limit switch may be configured to generate the first signal when the switch block is brought into contact with the limit switch during engagement of the first locking member and the second locking member.

The cradle transferring device may further comprise lifting and lowering means for lifting and lowering the shuttle table. The transfer member and the cradle may be joined and separated to and from each other by lifting and lowering the shuttle table. The limit switch may be configured to generate the second signal when the limit switch is brought into contact with the switch block during lifting the shuttle table.

A device for transferring a cradle for use with a PET-MRI hybrid system composed of a Positron Emission Tomography (PET) apparatus and a Magnetic Resonance Image (MRI) apparatus may also be provided. The cradle transferring device may comprise: a cradle having a first guide member lengthwisely disposed on a lower surface thereof, wherein a subject lies on an upper side thereof. Such a device may further comprise a shuttle table including: a transfer frame for supporting the lower side of the cradle; a transfer member for transferring the cradle, wherein the transfer member is mounted to the transfer frame so as to be movable along the transfer frame; a transfer member driving means for reciprocating the transfer member between a first position (where the transfer member is situated at one end of the transfer frame) and a second position (where the transfer member is situated at the other end of the transfer frame); a table cart reciprocating between the PET apparatus and the MRI apparatus while supporting the shuttle table so that the shuttle table can be lifted and lowered, wherein the table cart is situated adjacent to the MRI apparatus so that one end of an examination table of the MRI apparatus and the other end of the transfer frame are opposed to each other; a cradle receiving member located on the examination table of the medical imaging equipment for supporting the cradle transferred from the shuttle table, wherein the cradle receiving member has a second guide member lengthwisely disposed on an upper side thereof, the second guide member being configured to contact the first guide member; and a cradle locking means including a first locking member movably mounted to the cradle and a second locking member fixed to the cradle receiving member, wherein the first locking member is engaged and released to and from the second locking member.

One of the first and second guide members may include a plurality of rolling members, while the other may include a guide bar for contacting the rolling members.

The transfer member may have a holder for holding the cradle. Further, the cradle may have a holder engagement portion to which the holder is engaged.

The transfer member driving means may include: a first motor mounted to the shuttle table and producing normal and reverse rotations; and a belt winding along the transfer frame, where in the belt is driven by the first motor and joined to the transfer member.

The first locking member may comprise a shaft formed with a male thread at one end thereof. Further, the second locking member may comprise a nut formed with a female thread therein.

The cradle locking means may further include: a second motor mounted to the shuttle table and producing normal and reverse rotation; and a transmission member for transmitting the rotation of the second motor to the first locking member. The transmission member comprises a first transmission member disposed on the shuttle table in close proximity of one end of the shuttle table and a second transmission member disposed on the lower side of the cradle as joined together with the first locking member. When the transfer member is situated at the second position, the first transmission member and the second transmission member may be connected to each other. Further, the rotation of the second motor may be transmitted to the rotation of the first locking member.

The cradle transferring device may further comprise signal generating means for generating a first signal for stopping the second motor and a second signal for actuating the second motor.

The signal generating means may include a switch block disposed at the first locking member and a limit switch disposed at the one end of the transfer frame. The transfer member and the cradle may be joined and separated to and from each other by lifting and lowering the shuttle table after the cradle is transferred to the cradle receiving member. The limit switch may be configured to generate the first signal when the switch block is brought into contact with the limit switch during the engagement of the first and second locking members. The limit switch may be configured to generate the second signal when the limit switch is brought into contact with the switch block while lifting the shuttle table.

Any reference in this specification to "one embodiment," "an embodiment," "example embodiment," etc., means that a particular feature, structure or characteristic described in connection with the embodiment is included in at least one embodiment of the present invention. The appearances of such phrases in various places in the specification are not necessarily all referring to the same embodiment. Further, when a particular feature, structure or characteristic is described in connection with any embodiment, it is submitted that it is within the purview of one skilled in the art to effect such feature, structure or characteristic in connection with other ones of the embodiments.

Although embodiments have been described with reference to a number of illustrative embodiments thereof, it should be understood that various other modifications and embodiments can be devised by those skilled in the art that will fall within the spirit and scope of the principles of this disclosure. More particularly, numerous variations and modifications are possible in the component parts and/or arrangements of the subject combination arrangement within the scope of the disclosure, drawings and appended claims. In addition to variations and modifications in the component parts and/or arrangements, alternative uses will also be apparent to those skilled in the art.

What is claimed is:

1. A device for transferring a cradle for use with a medical imaging equipment, comprising:

a cradle having a first guide member lengthwisely disposed on a lower side thereof, wherein a subject lies on an upper side thereof;

a shuttle table including: a transfer frame for supporting the lower side of the cradle; a transfer member for transferring the cradle, wherein the transfer member is mounted to the transfer frame so as to be movable along the transfer frame; and a transfer member driving means for reciprocating the transfer member between a first position where the transfer member is situated at one end of the transfer frame and a second position where the transfer member is situated at the other end of the transfer frame, wherein the shuttle table is positioned so that one end of an examination table of the medical imaging equipment and the other end of the transfer frame are opposed to each other; and a cradle receiving member located on the examination table of the medical imaging equipment for supporting the cradle transferred from the shuttle table, wherein the cradle receiving member has a second guide member lengthwisely disposed on an upper side thereof, and wherein the second guide member is configured to contact the first guide member, wherein the device further includes a cradle locking means, and wherein the cradle locking means includes: a first locking member movably mounted to the cradle; and a second locking member fixed to the cradle receiving member, wherein the first locking member is engaged and released to and from the second locking member.

2. The device of claim 1, wherein the first locking member comprises a shaft formed with a male thread at one end thereof and the second locking member comprises a nut formed with a female thread therein.

3. The device of claim 2, wherein the cradle locking means further includes: a second motor mounted to the shuttle table and producing normal and reverse rotation; and a transmission member for transmitting the rotation of the second motor to the first locking member, wherein the transmission member comprises a first transmission member disposed on the shuttle table in close proximity of the one end of the transfer frame and a second transmission member disposed on the lower side of the cradle as joined together with the first locking member, and wherein when the transfer member is situated at the second position, the first transmission member and the second transmission member are connected to each other and the rotation of the second motor is transmitted to the rotation of the first locking member.

4. The device of claim 3, wherein the device further comprises signal generating means for generating a first signal for stopping the second motor and a second signal for actuating the second motor.

5. The device of claim 4, wherein the signal generating means includes a switch block disposed at the first locking member and a limit switch disposed at the one end of the transfer frame, and wherein if the switch block is brought into contact with the limit switch during an engagement of the first locking member and the second locking member, then the limit switch is configured to generate the first signal.

6. The device of claim 5, wherein the device further comprises lifting and lowering means for lifting and lowering the shuttle table, wherein the transfer member and the cradle are joined and separated to and from each other by lifting and lowering the shuttle table, and wherein if the limit switch is brought into contact with the switch block while lifting the shuttle table, then the limit switch is configured to generate the second signal.

7. A device for transferring a cradle for use with a PET-MRI hybrid system composed of a Positron Emission Tomography (PET) apparatus and a Magnetic Resonance Image (MRI) apparatus, comprising:

a cradle having a first guide member lengthwisely disposed on a lower side thereof, wherein a subject lies on an upper side thereof;

a shuttle table including: a transfer frame for supporting the lower side of the cradle; a transfer member for transferring the cradle, wherein the transfer member is mounted to the transfer frame so as to be movable along the transfer frame; and a transfer member driving means for reciprocating the transfer member between a first position where the transfer member is situated at one end of the transfer frame and a second position where the transfer member is situated at the other end of the transfer frame;

a table cart reciprocating between the PET apparatus and the MRI apparatus while supporting the shuttle table so that the shuttle table can be lifted and lowered, wherein the table cart is situated adjacent to the MRI apparatus so that one end of an examination table of the MRI apparatus and the other end of the transfer frame are opposed to each other;

a cradle receiving member located on the examination table of the MRI apparatus for supporting the cradle transferred from the shuttle table, wherein the cradle receiving member has a second guide member lengthwisely disposed on an upper side thereof, and wherein the second guide member is configured to contact the first guide member; and cradle locking means including a first locking member movably mounted to the cradle and a second locking member fixed to the cradle receiving member, wherein the first locking member is engaged and released to and from the second locking member.

8. The device of claim 7, wherein one of the first and second guide members includes a plurality of rolling members while the other includes a guide bar for contacting the rolling members.

9. The device of claim 7, wherein the transfer member has a holder for holding the cradle and the cradle has a holder engagement portion to which the holder is engaged.

10. The device of claim 7, wherein the transfer member driving means includes: a first motor mounted to the shuttle table and producing normal and reverse rotations; and a belt winding along the transfer frame, wherein the belt is driven by the first motor and being joined to the transfer member.

11. The device of claim 7, wherein the first locking member comprises a shaft formed with a male thread at one end thereof and the second locking member comprises a nut formed with a female thread therein.

12. The device of claim 11, wherein the cradle locking means further includes: a second motor mounted to the shuttle table and producing normal and reverse rotation; and a transmission member for transmitting the rotation of the second motor to the first locking member, wherein the transmission member comprises a first transmission member disposed on the shuttle table in close proximity of the one end of the transfer frame and a second transmission member disposed on the lower side of the cradle as joined together with the first locking member, and wherein when the transfer member is situated at the second position, the first transmission member and the second transmission member are connected to each other and the rotation of the second motor is transmitted to the rotation of the first locking member.

13. The device of claim 12, wherein the device further comprises signal generating means for generating a first signal for stopping the second motor and a second signal for actuating the second motor.

14. The device of claim 13, wherein the signal generating means includes a switch block disposed at the first locking member and a limit switch disposed at the one end of the transfer frame, wherein the transfer member and the cradle are joined and separated to and from each other by lifting and lowering the shuttle table after the cradle is transferred to the cradle receiving member, wherein if the switch block is brought into contact with the limit switch during an engagement of the first locking member and the second locking member, then the limit switch is configured to generate the first signal, and wherein if the limit switch is brought into contact with the switch block during lifting the shuttle table, then the limit switch is configured to generate the second signal.

* * * * *